(12) United States Patent
Bass

(10) Patent No.: US 6,900,047 B2
(45) Date of Patent: May 31, 2005

(54) APPARATUS FOR COATING A SUBSTRATE QUICKLY AND UNIFORMLY WITH A SMALL VOLUME OF FLUID

(75) Inventor: Jay K. Bass, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 314 days.

(21) Appl. No.: 10/174,406

(22) Filed: Jun. 17, 2002

(65) Prior Publication Data

US 2003/0064488 A1 Apr. 3, 2003

Related U.S. Application Data

(62) Division of application No. 09/494,187, filed on Jan. 28, 2000, now Pat. No. 6,406,851.

(51) Int. Cl.[7] ............................ C12M 1/34; C12Q 1/68; C12N 11/00; C07K 17/00; C07K 17/02
(52) U.S. Cl. .......................... 435/287.1; 435/6; 435/174; 435/177; 435/287.2; 435/287.3; 530/402; 530/810; 530/812
(58) Field of Search .............................. 435/6, 174, 177, 435/283.1, 287.1, 287.2, 287.3; 530/402, 810, 812

(56) References Cited

U.S. PATENT DOCUMENTS

| | | | |
|---|---|---|---|
| 4,596,695 A | 6/1986 | Cottingham | 422/58 |
| 5,145,784 A | 9/1992 | Cox et al. | 436/526 |
| 5,256,535 A | 10/1993 | Ylikoski et al. | 435/6 |
| 5,622,822 A | 4/1997 | Ekeze et al. | 435/6 |

*Primary Examiner*—David M. Naff

(57) ABSTRACT

A method is provided for applying a fluid onto a surface of a solid substrate. The method employs a distribution member having an upper surface and a lower surface, and including a permeable portion having channels therethough. The distribution member is positioned such that the lower surface of the distribution member is in opposing relation to the surface of the substrate. Once the distribution member is in position, the fluid is dispensed onto the upper surface of the permeable portion of the distribution member such that the fluid penetrates the distribution member and is retained thereby. In addition, a distribution pressure differential is applied between the upper and lower surfaces without using mechanical means such as a squeegee so that a portion of the fluid passes through the channels of the permeable portion of the distribution member and onto the solid substrate surface. Other embodiments of the invention include an apparatus for carrying out the aforementioned method and a reagent application station for applying a plurality of reagents onto a surface of a solid substrate.

21 Claims, 2 Drawing Sheets

US 6,900,047 B2

APPARATUS FOR COATING A SUBSTRATE QUICKLY AND UNIFORMLY WITH A SMALL VOLUME OF FLUID

This is a Divisional of application Ser. No. 09/494,187, filed on Jan. 28, 2002 now U.S. Pat. No. 6,406,851 B1, the entire disclosure of which is incorporated herein by reference.

TECHNICAL FIELD

This invention relates generally to a method and apparatus to coat a substrate with a small volume of fluid. More particularly, the invention relates to a method and apparatus to quickly and uniformly coat a fluid such as reagents or fluids used in DNA array fabrication onto a surface of a solid substrate by providing a pressure differential between substantially parallel surface of a fluid-containing distribution member.

BACKGROUND

Nucleic acid hybridization is a known method for identifying specific sequences of nucleic acids; hybridization involves base-pairing between complementary nucleic acid strands. When single-stranded nucleic acids are used as probes to identify specific target sequences of nucleic acids, probes of known sequences are exposed to and incubated in sample solutions containing sequences to be identified. If a sequence hybridizes to a probe of a known sequence, the sequence is necessarily the specific target sequence. Various aspects of this method have been studied in detail. In essence, all variations allow complementary base sequences to pair and thus form double-stranded stable molecules, and a variety of methods are known in the art to determine whether pairing has occurred, such as those described in U.S. Pat. No. 5,622,822 to Ekeze et al. and U.S. Pat. No. 5,256,535 to Ylikoski et al.

Hybridization of surface-bound probes to solution-based targets is an effective means to analyze a large number of DNA or RNA molecules in parallel. Specific probes of known sequences are attached to the surface of a solid substrate in known locations. The probes are usually immobilized on a solid support having a surface area of typically less than a few square centimeters. The solid support is typically a glass or fused silica slide which has been treated to facilitate attachment of probes. A mobile-phase sample containing labeled targets, e.g., a buffered aqueous solution containing target DNA, is contacted with and allowed to react with the surface. By detecting the labels to determine whether hybridization has occurred at specific locations, it is possible to determine the composition of the sample and the sequences of the unknown targets. Alternatively, target biomolecules may be bound to the surface while labeled probes are contained in the mobile phase. In either case, the hybridization reaction typically takes place over a time period that can be many hours, for a typical sample containing target material in the concentration range in the picomolar domain.

In the preparation of arrays such as those for use in nucleic acid hybridization, reagents may be applied to predetermined locations on the surface of a substrate. Generally, a surface is first cleaned or otherwise prepared by exposure to a fluid containing a reagent. Then, array preparation will involve application of biomolecule-containing fluids at discrete locations. For nucleic-acid probe array preparation, the biomolecule-containing fluid may contain the already-formed probes that can bind with the surface, or a specific nucleotide that will later constitute a portion of a probe that is synthesized in situ on the surface. Then, treatment of a portion of or the entire surface with a different fluid may follow. The steps may be repeated a number of times in situ to prepare the desired array. Once an array of probes is formed on a substrate surface for hybridization with target molecules in a sample fluid, hybridization may be carried out by uniformly exposing the entire substrate surface to the sample fluid.

It is apparent, then, that surface coating by a fluid is an important aspect in array technology, particularly in the field of biomolecular arrays. Important aspects of coating procedures include the amount of fluid used and the rate of throughput. In general, coating procedures should employ only a small quantity of fluid, for a number of reasons. First, the fluid may contain expensive or rare reagents, and waste of such fluids is undesirable. Second, many ordinary reagents that are used in array preparation are toxic, and decreasing their use is desirable in order to lower the risk of human exposure. A high throughput rate also implies that it takes less time to coat each substrate surface, thereby also lowering the risk of human exposure during the coating procedure.

Another important aspect of coating procedures is uniformity of coverage. For biomolecular arrays, it is desirable to uniformly apply a fluid onto a substrate surface to ensure that each feature is attached or formed under similar conditions. In addition, during use of a formed array containing surface-bound probes, uniform distribution of sample fluid to ensure proper hybridization is necessary. Without uniform fluid distribution, resultant hybridization data will be compromised.

One method by which a surface may be coated with a small amount of fluid is through the use of a flow cell assembly. Variations on the use of a flow cell are described in U.S. Pat. Nos. 4,596,695 to Cottingham and 5,145,784 to Cox et al. The basic flow cell method typically provides that a cover and substrate are positioned parallel to each other. A gap is thus formed between the cover and the substrate. To control the size of the gap, one or more spacers having a selected height are disposed within the gap. In addition, the cover, the spacers and the substrate are arranged such that a chamber is provided having an inlet channel and an outlet channel. By creating an appropriate pressure gradient between the inlet and outlet channels, fluid fills the chamber by laminar flow, coating the surface of the substrate within the chamber. By controlling the volume in the chamber through the proper selection of the spacer height, the amount of fluid needed to coat the surface can be reduced.

The use of the flow cell method has a number of drawbacks. First, uniform coating requires laminar flow of the fluid. Laminar flow regime generally implies that there is an absolute upper limit to the volumetric rate given the geometry of the chamber. Second, to increase the flow rate of the fluid, the pressure gradient between the inlet and outlet channels must be increased. However, pressure surges that are generated while increasing the pressure gradient tend to cause the flow cell assembly to leak, either at the cover/support interface or at the support/substrate interface. Third, any irregularity in the surface profile of the substrate tends to disrupt laminar flow. As a result, air pockets may be formed and trapped within the flow cell assembly that will interrupt contact between the fluid and the substrate. Thus, while the use of a flow cell tends to lower the amount of reagent fluid waste, the gain in lowered waste is offset by diminishing throughput.

Spin coating may be employed to quickly and uniformly coat a fluid on a substrate. Spin coating is usually performed by dispensing the fluid at or near the center of a substrate. The substrate is spun either during or after the reagent is dispensed such that the fluid spreads radially and outwardly to cover the entire substrate. In this method, the volume needed to cover a surface depends on fluid property, e.g., viscosity and surface tension, and the surface energy of the substrate. When a low energy surface is provided, a relatively large volume fluid is needed to cover the entire surface. Without sufficient volume, applied fluid tends to exhibit clustering behavior and does not cover the entire surface uniformly. Thus, a relatively large amount of fluid is first applied to the surface at a low spin speed to cover the entire surface. Then, the substrate is spun at a higher speed to remove excess fluid. Consequently, while spin coating may be advantageous in terms of high throughput, it is a relatively wasteful technique.

Thus, there is a need to provide a method and apparatus to coat a substrate surface with a small volume of fluid quickly and uniformly without relying on spin coating or an ordinary flow cell.

SUMMARY OF THE INVENTION

Accordingly, it is an object of the present invention to overcome the above-mentioned disadvantages of the prior art by providing a method for coating a substrate surface with a small volume of fluid without generating excess waste.

It is another object of the invention to provide such a method wherein the substrate is coated quickly and uniformly.

It is still another object of the invention to provide an apparatus for use in carrying out the aforementioned method.

It is a further object of the invention to provide such an apparatus for use in carrying out the aforementioned method with a plurality of fluids in succession.

Additional objects, advantages and novel features of the invention will be set forth in part in the description which follows, and in part will become apparent to those skilled in the art upon examination of the following, or may be learned by practice of the invention.

In one general aspect, then, the present invention relates to a method for applying a fluid onto an application area located on a surface of a solid substrate. The method comprises providing a distribution member having an upper surface and a lower surface, and including a permeable portion having channels of a selected size. The distribution member may be generally planar and is positioned such that the lower surface of the distribution member is in generally opposing spacing relation to the surface of the substrate. The distribution member and the substrate may also be substantially uniformly spaced relation. A predetermined volume of the fluid is dispensed onto the upper surface of the permeable portion of the distribution member such that the fluid penetrates and is retained by the permeable portion of the distribution member. The fluid may penetrate and be retained by the permeable portion of the distribution member under the application of a loading pressure differential between the upper and lower surfaces. In addition, a distributing pressure differential is applied between the upper and lower surfaces generally without using a movable mechanical means designed to spread fluids such as a squeegee such that at least a portion of the fluid passes through the channels of the permeable portion of the distribution member and onto the application area. The application area may contain any array of biomolecules covalently or otherwise attached thereto.

In another aspect, the invention relates to the above method wherein a perimeter spacer is provided and positioned between and in contact with the lower surface of the distribution member and the surface of the solid substrate. Accordingly, the perimeter spacer defines an application volume between the lower surface of the distribution member and the surface. The fluid passes through the channels of the permeable portion of the distribution member and into the application volume.

In still another aspect, the invention relates to the above method wherein the distribution pressure differential is generated by raising the pressure at the second surface of the distribution member. The distribution pressure differential may also be generated by lowering the pressure at the lower surface of the distribution member.

In a further aspect, the invention relates to the above method further comprising the step of dispensing a second fluid onto the upper surface of at least the permeable portion of the distribution member. A pressure differential between the upper and lower surfaces is applied such that the second fluid passes through the channels in the permeable portion of the distribution member and onto the application area, displacing the fluid away from the solid substrate surface. In addition, the method may further comprise the step of flushing a gas through the permeable portion of the distribution member such that the second fluid is displaced away from the solid substrate surface. The gas may comprise nitrogen or argon.

In a still further aspect, the invention relates to the above method wherein the fluid contains water, or an organic solvent such as acetonitrile, an alcohol, or a ketone. Likewise, the fluid may comprise a biomolecule. Examples of biomolecules include oligonucleotides, polynucleotides, oligopeptides and polypeptides. In order to prevent fluid waste, it is preferred that the predetermined volume of the fluid does not substantially exceed the application volume. More preferably, the predetermined volume of the fluid should not exceed about 150% of the application volume. Still more preferably, the predetermined volume should not exceed about 110% of the application volume.

In another general aspect, the invention relates to an apparatus for applying a fluid onto a surface of a solid substrate. The apparatus comprises a distribution member having an upper surface, a lower surface and a permeable portion formed by a plurality of channels extending from the upper surface to the lower surface. Such a distribution member may comprise a perforated flat piece or a mesh. Affixed in sealed contact with the upper surface about the permeable portion of the distribution member is an enclosing wall that, together with the distribution member, defines an enclosure having an enclosure volume. The apparatus also provides means for positioning the distribution member in relation to the solid substrate surface such that the lower surface of the distribution member is in generally uniformly spaced opposing relationship to the solid substrate. Once fluid is introduced onto the fluid distribution area within the enclosure, a means for producing a positive pressure differential between the upper surface and the lower surface of the distribution member can be activated. As a result, the liquid passes through the member and onto the solid substrate surface.

In another aspect, the invention relates to the above apparatus wherein a spacer having generally parallel upper and lower surfaces is provided. In such a case, the upper surface of the spacer is affixed to the lower surface of the distribution member about the permeable portion. The lower surface is placed in contact with the substrate such that an application space having an application volume is substantially enclosed by the spacer, the lower surface of the distribution member, and the substrate surface. An opening may be disposed in the spacer such that the application space fluidly communicates with open air. In order to prevent fluid waste, it is preferred that the enclosure volume does not substantially exceed the application volume. More preferably, the enclosure volume should not exceed about 150% of the application volume. Still more preferably, the enclosure volume should not exceed about 110% of the application volume.

In still another aspect, the invention relates to the above apparatus wherein the means for introducing the fluid comprises a fluid source for supplying the fluid. A fluid transfer channel is connected to the enclosure and, a fluid valve is disposed between the fluid source and the fluid transfer channel. Fluid communication is provided from the fluid source to the fluid transfer channel when the fluid valve is open. In addition, the apparatus may include means for introducing a second fluid. Such means may comprise a second fluid source for supplying the second fluid and a second fluid valve disposed between the second fluid source and the fluid transfer channel, where the second fluid source is in fluid communication with the fluid transfer channel when the second fluid valve is open. In any case, the fluid may contain a liquid such as water, acetonitrile, an alcohol, or a ketone for use in facilitating chemical reactions. Where hybridization reactions are desired, the fluid will contain a biomolecule such as an oligonucleotide, polynucleotide, oligopeptide, or polypeptide.

In a further aspect, the invention relates to the above apparatus wherein the means for producing a pressure differential may comprise means for raising pressure within the chamber. Such pressure raising means may comprise means for introducing a gas into the enclosure from a pressured source. The gas may comprise, for example, nitrogen or argon.

In still another general aspect, the invention relates to a reagent application station for applying a plurality of reagents onto a surface of a solid substrate. The apparatus comprises a distribution member having an upper surface, a lower surface and a permeable portion formed by a plurality of channels extending from the upper surface to the lower surface. An enclosure is formed by the upper surface of the distribution member and an enclosing wall affixed about the permeable portion in sealed contact with the upper surface of the distribution member. The apparatus also provides means for positioning the distribution member in relation to the solid substrate surface such that the lower surface of the distribution member is in generally uniformly spaced opposition relation to the solid substrate. To control pressure within enclosure, a variable pressure pump is provided having an inlet for each reagent and an outlet in fluid communication with the enclosure. To supply the reagents, a source for each reagent is provided, and a valve is disposed between each inlet and source to provide individual control over fluid dispensing. It is preferred that no two valves are open at the same time.

BRIEF DESCRIPTION OF THE FIGURES

The invention is described in detail below with reference to the following drawings.

DETAILED DESCRIPTION OF THE INVENTION

Figure 1:
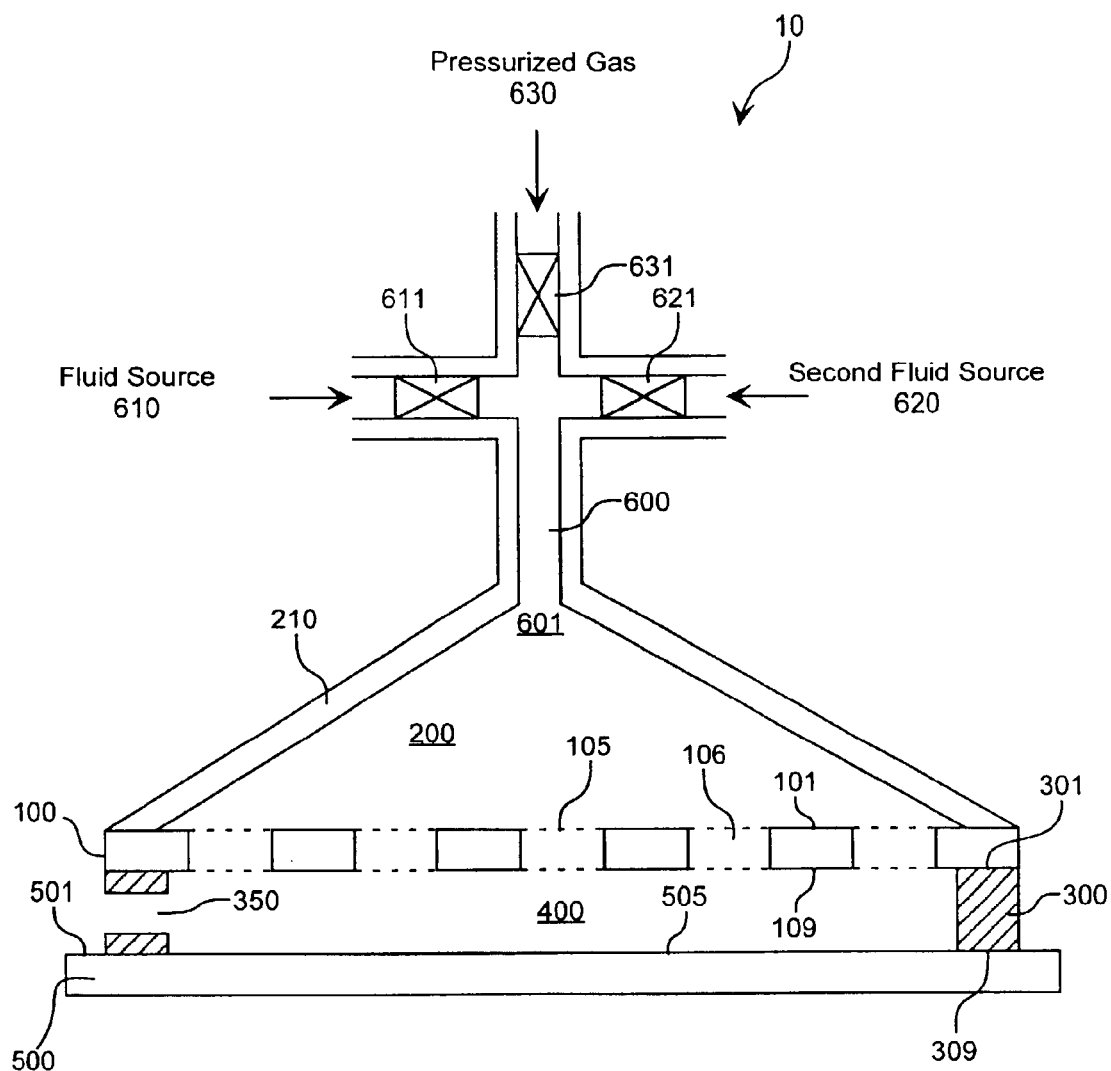
FIG. 1 schematically illustrates an apparatus of the present invention.

Before describing the invention in detail, it must be noted that, as used in this specification and the appended claims, the singular forms "a," "an," and "the" include plural referents unless the context clearly dictates otherwise. Thus, for example, reference to "a fluid" includes more than one fluid, reference to "a biomolecule" includes a plurality of biomolecules, reference to "a fluid source" includes a plurality of fluid sources and the like.

In describing and claiming the present invention, the following terminology will be used in accordance with the definitions set out below.

The terms "array" is used herein to refer to an ordered pattern of features, typically but not necessarily biomolecules, adherent to a substrate, e.g., a plurality of molecular probes bound to a substrate surface and arranged in a spatially defined and physically addressable manner. Such probes may be comprised of oligonucleotides, peptides, polypeptides, proteins, antibodies, or other molecules used to detect sample molecules in a sample fluid.

The term "biomolecule" as used herein refers to an organic molecule that may be found in a living organism or synthetically produced. Typically, biomolecules are large and may have a complementary counterpart. Examples of biomolecules include but are not limited to nucleotidic molecules such as oligonucleotides and polynucleotides and peptidic molecules such as oligopeptides and polypeptides.

The term "feature" refers to an element or a constituent part of matter forming a pattern situated on a surface. As used herein, features can be deposited, dispensed, printed, placed, positioned or otherwise disposed on a surface.

The term "fluid" as used herein refers to a material that is not purely gaseous which tends to flow to conform to the outline of its container. Unless otherwise stated, the fluids described herein comprise a liquid and may contain solvated gas or fully solvated, partially solvated or suspended solids.

The term "hybridization" as used herein means binding between complementary or partially complementary molecules, as between the sense and anti-sense strands of double-stranded DNA. Such binding is commonly non-covalent in nature, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "monomer" as used herein refers to a chemical entity that can be covalently linked to one or more other such entities to form an oligomer. Examples of "monomers" include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid surface chain, a nucleotide base, etc.). The initial substrate-bound monomer is generally used as a building-block in a multi-step synthesis procedure to form a complete ligand, such as in the synthesis of oligonucleotides, oligopeptides, and the like.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Moreover, the terms "nucleoside" and "nucleotide" include functional analogs (whether synthetic or naturally occurring) of such sub units which in the polymer form (as a polynucleotide) can hybridize with naturally occurring polynucleotides in a sequence specific manner analogous to that of tow naturally occurring polynucleotides. For example, these include the sub-units of PNA and other polynucleotides as described in U.S. Pat. No. 5,948,902 and references cited therein (all of which are incorporated herein by reference), regardless of the source.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides, polyribonucleotides, other polynucleotides which are—or C-glycosides of a purine or pyrimidine base, polypeptides, polysaccharides, and other chemical entities that contain repeating units of like chemical structure.

The term "probe" as used herein means a biomolecule of known identity that is typically but not necessarily adherent to a substrate or a base member of a hybridization package.

The term "reagent" as used herein means a substance used in the preparation of an array on a surface because of its chemical or biological activity. Typically, reagents as used herein refer to liquid compounds or solutions involved the synthesis of biomolecular arrays and include, but are not limited to: acetonitrile; buffered solutions containing biomolecules; mecaptosilane containing solutions; aqueous iodine solutions; alcohols; acids; bases; oxidizing agents; reducing agents; organic or inorganic fluids for deprotection reactions employed in in situ DNA synthesis; etc.

The term "sample" as used herein relates to a material or mixture of materials, at least partially in fluid form, containing one or more components of interest.

The term "squeegee" as used herein means an implement having an elastic surface that is used in printing for spreading, pushing, or wiping a liquid material on, across, or off a surface. Unless otherwise specified, "squeegeeless means" as used herein refer to a means that excludes the substantial participation of a blade or other like solid component for spreading, pushing, or wiping of a liquid material by direct mechanical action.

The term "target" refers to a known or unknown molecule in a sample, which will hybridize to a probe if the target molecule and the molecular probe contain complementary regions. In general, the target molecule is a "biopolymer," i.e., an oligomer or polymer such as an oligonucleotide, a peptide, a polypeptide, a protein, an antibody, or the like.

The present invention in general terms is directed to a method for applying a fluid onto an application area on a surface of a solid substrate. Unlike previous methods such as spin coating or flow cell techniques, the present method provides for fast and controlled delivery of a fluid to coat a surface with little if any waste of the fluid. The method employs a generally planar distribution member to hold a predetermined volume of the fluid above the application area. Without the use of a direct mechanical action by a solid component such as a squeegee, a pressure differential is applied between the upper and lower surfaces of the member to effect flow of the fluid onto the application area of the surface.

The invention is described herein with reference to the figures. The figures are not to scale, and in particular, certain dimensions may be exaggerated for clarity of presentation. FIG. 1 schematically illustrates an apparatus of the present invention. As shown, the apparatus 10 comprises a distribution member 100 having an upper surface 101 and a lower surface 109. The distribution member includes a permeable portion 105 with a plurality of channels 106 therethrough. The channels provide communication between the upper and lower surfaces of the distribution member. The apparatus also comprises an enclosure 200 formed by a tapered cone-shaped wall 210 affixed about the permeable portion and in sealed relation to the upper surface of the distribution member. As shown, the apparatus 10 further comprises a spacer 300 having a generally parallel upper surface 301 and lower surface 309. The upper surface of the spacer is affixed to the lower surface of the distribution member about the permeable portion. The lower surface of the spacer is placed in contact with an upper surface 501 of a solid substrate 500. This is done by using means (not shown) for positioning the distribution member in relation to the solid substrate surface such that the lower surface of the distribution member is in generally uniformly spaced opposing relation to the solid substrate. Such means are known to one of ordinary skill in the art and include, but are not limited to, pulleys, levers, gears, and combinations thereof. In particular, indexing means typically used in semiconductor wafer processing may be employed to control positioning with precision and accuracy. Typically, a chuck of some type (not shown), e.g., vacuum, electrostatic, mechanical, etc., is used to render the solid substrate immobile while the distribution member is positioned to ensure proper alignment with the substrate surface. As a result, the lower surface of the distribution member, the spacer, and the substrate substantially enclose an application space 400. An optional hole 350 is provided in the spacer such that an application area 505 located on the surface within the application space fluidly communicates with open air. The application area is the area on the surface of the substrate where desired reagents are applied in order to carry out desired reactions. Examples of such reactions include, but are not limited to, functionalization of the surface, in situ chemical synthesis such as of biomolecules in an array, and hybridization of surface bound probes with a sample fluid containing target biomolecules. It is envisioned that the fluid may be applied to the application area before, during, or after the formation of a particular biomolecular array and that the features of the array may be attached to the application area by covalent bonding, electrostatic bonding, polar attraction, Van Der Waal's forces or other approaches known to one of ordinary skill in the art.

As shown, the enclosure formed by the wall 210 is generally in the form of a cone. For such a conically shaped enclosure, the angle between the enclosing wall and the distribution member, i.e., the base and the surface of the cone, can be any acute angle between 0° and 90°. It is expected that an angle of about 10 to about 30° is preferred due to fluid flow, geometric and volume consideration. An angle of about 10 to about 20° is more preferred, and about 15° should provide optimal results. As shown, a transfer port 601 is disposed on the enclosing wall. Extending from the transfer port is a fluid transfer channel 600. The apparatus also provides for a source 610 of a fluid. A fluid valve is positioned between the fluid source and the fluid transfer channel such that when the fluid valve is open, the fluid source is in fluid communication with the fluid transfer channel, which in turn, fluidly communicates with the enclosure 200. Preferably, the fluid source imposes a loading pressure on the fluid such that when the fluid valve is open, the fluid flows from the source and fills the enclosure, thereby contacting the upper surface of the distribution member. The loading pressure also effects penetration or retention of the fluid by the distribution member. Once penetration and retention have been achieved, the fluid valve is closed.

The apparatus also provides for a source of pressurized gas 630. Disposed between the pressurized gas source and the fluid transfer channel is a gas valve 631 that can regulate the pressure of the gas from the gas source. When the gas valve is open such that fluid communication is provided between the gas source and the enclosure, the pressurized gas is forced through the fluid transfer channel and into the enclosure. As a result, pressure within the enclosure is raised with respect to the pressure at the lower surface of the distribution member, and at least a portion of the fluid passes through the channels of the permeable portion of the distribution member and onto the application area within the application volume. When the application volume 400 is filled, the combination of the pressure from the pressurized gas and the physical contact between the distribution member and the fluid ensures that all of the application area is substantially equivalently exposed to the fluid. No squeegee or other like means is employed or necessary in this process to induce the pressure differential between the upper and lower sides of the distribution member. Once sufficient time has passed, the gas valve may be opened further such that gas is flushed through the permeable portion of the distribution member and at least a portion of the fluid is thereby displaced away from the solid substrate surface.

Particularly in biomolecular array applications, it is a requirement that the gas used is pure, i.e., does not contain any contaminants or impurities that could interfere with the function of the fluid. Particulate matter is particularly problematic because such matter may become lodged in the distribution member, thereby adversely affecting fluid flow. Suitable gases include, but are not limited to air, nitrogen, argon and other inert gases.

Where it is desired to apply a second fluid after the application of the initial fluid, a second fluid source 620 is provided as shown in FIG. 1. Disposed between the second fluid source and the fluid transfer channel is a second fluid valve 621. After the initial fluid is displaced away from the solid substrate surface, the second fluid valve is opened to render the second fluid source in fluid communication with the fluid transfer channel. Preferably, the second fluid source, like the fluid source, also imposes a loading pressure on the second fluid such that when the second fluid valve is open, the second fluid flows from its source, fills the enclosure, and contacts the upper surface of the distribution member. The loading pressure also facilitates penetration and retention of the second fluid by the distribution member. Once penetration and retention have been achieved and the second fluid valve is closed, gas is introduced into the enclosure to cause the second fluid to flow onto the application area within the application volume. In the alternative, the second fluid may be a wash fluid that is flushed through the permeable portion of the distribution member to displace the fluid from the surface of the solid substrate.

It is evident, then, that a method of applying one or more fluids is provided. One step of the method involves applying a distribution pressure differential between the upper and lower surfaces of the distribution member for each fluid. Such differential can be applied in a number of ways. For example, pressure at the upper surface of the distribution member may be raised. In addition, pressure at the lower surface of the distribution member may be lowered. Furthermore, a combination of pressure raising at the upper surface of the distribution member and pressure lowering at the lower surface of the distribution member may be employed. Means for controlling pressure usually involve the use of a pump as is generally known in the art.

It is also evident that the invention encompasses a reagent application station for applying a plurality of reagent fluids onto a surface of a solid substrate. The station comprises: a distribution member having an upper surface, a lower surface and a permeable portion formed by a plurality of channels extending from the upper surface to the lower surface; an enclosure formed by an enclosing wall affixed about the permeable portion in sealed contact with the upper surface of the distribution member; and means for positioning the distribution member in relation to the solid substrate surface such that the lower surface of the distribution member is in generally uniformly spaced opposition relation to the solid substrate. The station also comprises a source for each reagent; a variable pressure pump having an inlet for each source and an outlet in fluid communication with the enclosure; and a valve between each inlet and each source. The variable pressure pump should be capable of generating at least two pressures within the enclosure to effect loading of fluid into the distribution member and dispensing of fluid onto the application area of the substrate surface as described above. Such a pump may be able to provide a continuous range of pressures within the enclosure. It is also preferred that no two valves are open at the same time, to prevent cross-contamination of the sources. Such a condition can be imposed on the station by computerized means known in the art. In addition, computerized means can be used to ensure that the reagents are dispensed in a desired sequence.

Although the invention is adaptable for use to distribute a small amount of fluid in a variety of applications and to cover surfaces of any size, the invention is particularly useful in lowering fluid waste in a device for forming biomolecular arrays. The geometry, size constraints and other limitations of such a device make it difficult to employ ordinary silkscreening methods that use a squeegee to coat a surface with a fluid. The ordinary biomolecular array device may comprise a substrate having a contact area in any shape including without limitation, square, rectangular, circular, etc. Substrates having a 3" by 3" inch contact area and substrates having a 6" by 6" contact area have been produced. The distance between distribution member and the contact area is ordinarily on the order of about 100 microns. However, the distance may be as low as about 5 microns to as high as about 3000 microns and may be controlled by the height of the spacer, i.e., the distance between the generally parallel upper and lower surface of the spacer. The critical factor in determining the distance is the volume of fluid or reagent needed to effect the desired result. That volume can be readily determined. As is apparent from FIG. 1, the application volume is dependent on the contact area and the distance between the distribution member and the contact area. To lower the amount of fluid waste, it is preferred that for any application of a particular volume of the fluid, the volume does not substantially exceed the application volume. It is particularly preferred that the volume of the fluid is no more than about 150% of the application volume. Optimally, the volume of the fluid is no more than about 110% of the application volume. In addition, the enclosure volume may correspond to the application volume such that the enclosure volume does not substantially exceed the application volume.

Figure 2A:
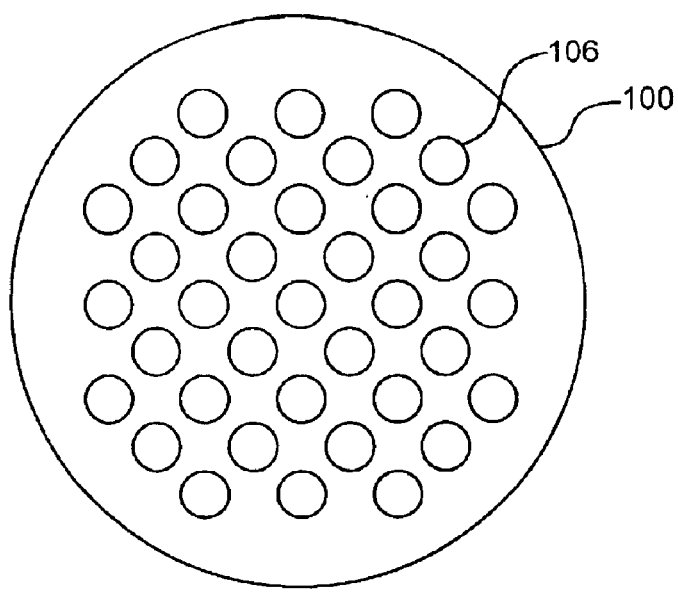
FIGS. 2A and 2B illustrate alternative embodiments of the distribution member suitable for use in an apparatus of the invention.
Figure 2B:
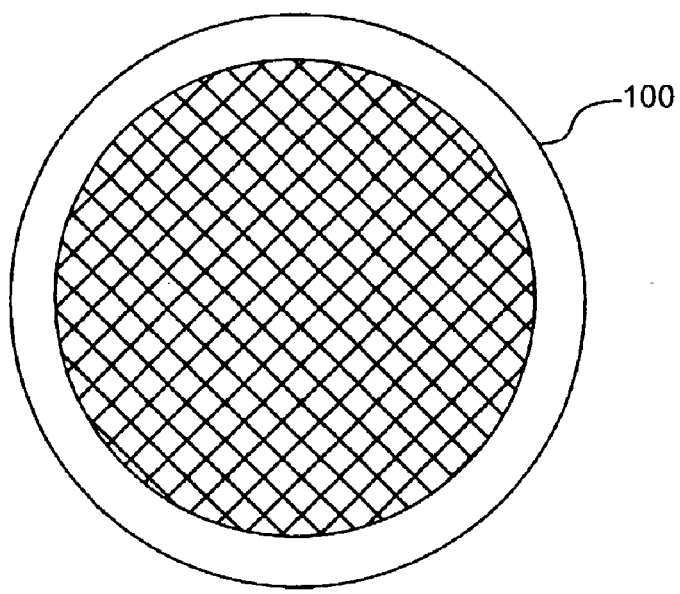

The distribution member is now described. The distribution member may be any of a variety of shapes. However, it is preferred that the distribution member be generally planar with roughly parallel upper and lower surfaces. The distribution member must include a permeable portion with a plurality of channels therethrough that provide communication between the upper surface and the lower surface. Thus, the channels terminate in openings on the upper and lower surfaces of the distribution member. The cross-sectional area of the channels and their terminal channels are typically small for a number of reasons. First, a fluid dispensed on the upper surface will immediately pass through the permeable portion of the distribution member if the channels are too large. User control of the rate and the manner of fluid distribution is thereby compromised. In addition, it is important to keep in mind the invention may be adapted to apply a very small amount of fluid to coat a surface. Depending on the surface properties of a particular fluid and substrate surface, the fluid may tend to form beads on the substrate. Therefore, the lower surface of the distribution member may be used to mechanically ensure that the distributed fluid uniformly contacts the contact area of the substrate surface. Holes with large diameters and excessively long channels may render the distribution member incapable of serving this function. Possible versions of the distribution member are illustrated in FIGS. 2A and 2B. FIG. 2A illustrates a flat piece 100 that is perforated with circular channels 106 extending from one parallel surface to another. FIG. 2B illustrates a distribution member having a permeable portion comprising a mesh.

When a small amount of fluid is to be applied, surface forces become increasingly important. Thus, the material of the distribution member should be chosen according to the fluid or fluids to be used. While the invention may be adapted to apply any number of fluids, typical fluids that are used in the formation of biomolecular arrays include, but are not limited to, those that contain: water; acetonitrile; alcohols such as methanol, ethanol, propanol, isopropanol, and ethylene glycol; and ketones such as acetone and methyl ethyl ketone. In addition, such fluids may contain biomolecules such as oligonucleotides, polynucleotides, oligopeptides and polypeptides. As a basic requirement, the material from which the distribution member is made must be dimensionally stable to exposure with the components of the fluid or fluids used, if the distribution member is to be used more than once. In addition, the material should obviously not impart any undesired contaminants into fluid. For example, when acetonitrile is used as a solvent, the distribution member should not be made with a flat perforated piece of polystyrene, since polystyrene is soluble in acetonitrile. In addition, due to the quantity of fluid involved, the material should be selected to take advantage of its intrinsic surface properties with respect to the fluid to be dispensed. For example, if the fluid contains water, the distribution member may be made from a hydrophobic material such as polytetrafluoroethylene to ensure that fluid does not wick toward the distribution member from the contact area of the substrate surface. As will be evident to one of ordinary skill in the art, coatings may also be applied at specific areas on the distribution member to selectively control the wetting properties of the specific areas. As a general rule, ceramic and metallic materials are suitable for use in distribution members because they are stable with respect to many fluids and it is possible to make a perforated flat piece having channels with precision needed to render the invention operative. Certain polymers that are resistant to solvents may also be a suitable material.

Variations of the foregoing will be apparent to those knowledgeable in the art. For example, if a plurality of fluids is dispensed, the apparatus may include more than one fluid transfer channel connected to the enclosure. In other words, variations known to one of ordinary skill in means of conveying fluids from their sources to the enclosure may be employed. As another example, a sealing material may be provided and disposed between two components of the apparatus if sealing contact is made. As still another example, fastening means may be employed if two components of the invention are affixed to one another.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

What is claimed is:

1. An apparatus for applying a fluid onto a surface of a solid substrate, comprising:

a distribution member having an upper surface, a lower surface and a permeable portion formed by a plurality of channels extending from the upper surface to the lower surface;

an enclosure having an enclosure volume formed by an enclosing wall affixed about the permeable portion in sealed contact with the upper surface of the distribution member;

a spacer for positioning the distribution member in relation to the solid substrate surface such that the lower surface of the distribution member is in opposing relation to the solid substrate thereby providing an application volume;

means for introducing the fluid on to the upper surface of the distribution member within the enclosure; and means for producing a pressure differential between the upper surface and the lower surface of the distribution member without using a squeegee, whereby the pressure differential causes a portion of the fluid to pass through the member and onto solid substrate surface.

2. The apparatus of claim 1 wherein said spacer comprises, an upper surface and a lower surface, the upper spacer surface affixed to the lower surface of the distribution member about the permeable portion and the lower spacer surface in contact with the substrate surface, such that an application space having an application volume is substantially enclosed by the spacer, the lower surface of the distribution member and the substrate surface.

3. The apparatus of claim 2 wherein the upper spacer surface and the lower spacer surfaces are generally parallel surfaces of the spacer.

4. The apparatus of claim 2, further comprising an opening in the spacer such that the application space fluidly communicates with open air.

5. The apparatus of claim 2, wherein the enclosure volume is not substantially greater than the application volume.

6. The apparatus of claim 1, wherein the enclosure volume is no more than about 150% of the application volume.

7. The apparatus of claim 6, wherein the enclosure volume is no more than about 110% of the application volume.

8. The apparatus of claim 1, wherein the distribution member is generally planar.

9. The apparatus of claim 1, wherein the distribution member is substantially flat and perforated.

10. The method of claim 1, wherein the distribution member comprises a mesh.

11. The apparatus of claim 1, wherein the means for introducing the fluid comprises a fluid source for supplying the fluid, a fluid transfer channel connected to the enclosure and a fluid valve disposed between the fluid source and the fluid transfer channel, wherein the fluid source is in fluid communication with the fluid transfer channel when the fluid valve is open.

12. The apparatus of claim 11, further comprising means for introducing a second fluid, wherein the means for introducing the second fluid comprises a second fluid source for supplying the second fluid and a second fluid valve disposed between the second fluid source and the fluid transfer channel, wherein the second fluid source is in fluid communication with the fluid transfer channel when the second fluid valve is open.

13. The apparatus of claim 11, wherein the means for producing a pressure differential comprises a gas source for supplying the gas and a gas valve disposed between the gas source and the fluid transfer channel, wherein the gas source is in fluid communication with the fluid transfer channel when the gas fluid valve is open.

14. The apparatus of claim 1, wherein the means for producing a pressure differential comprises means for raising pressure within the enclosure.

15. The apparatus of claim 14, wherein the pressure raising means comprises means for introducing a gas into the enclosure from a pressured source.

16. The apparatus of claim 15, wherein the gas comprises nitrogen or argon.

17. The apparatus of claim 1, wherein the fluid comprises water, acetonitrile, an alcohol, or a ketone.

18. The apparatus of claim 1, wherein the fluid contains a biomolecule.

19. The apparatus of claim 18, wherein the biomolecule is an oligonucleotide, polynucleotide, oligopeptide, or polypeptide.

20. A reagent application station for applying a plurality of reagents onto the surface of a solid substrate, comprising:
 a distribution member having an upper surface, a lower surface and a permeable portion formed by a plurality of channels extending from the upper surface to the lower surface;
 an enclosure having an enclosure volume formed by an enclosing wall affixed about the permeable portion in sealed contact with the upper surface of the distribution member;
 a spacer for positioning the distribution member in relation to the solid substrate surface such that the lower surface of the distribution member is in generally uniformly spaced opposition relation to the solid substrate thereby providing an application volume;
 a source for each reagent;
 a variable pressure pump having an inlet for each source and an outlet in fluid communication with the enclosure; and
 a valve between each inlet and each source.

21. The reagent application station of claim 20, wherein no two valves are open at the same time.

* * * * *